US00PP18549P2

(12) United States Plant Patent
Utecht

(10) Patent No.: US PP18,549 P2
(45) Date of Patent: Mar. 4, 2008

(54) *PELARGONIUM* PLANT NAMED 'FISBURG'

(50) Latin Name: *Pelargonium peltatum L'Héritier*
Varietal Denomination: Fisburg

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 11/529,119

(22) Filed: Sep. 28, 2006

(51) Int. Cl.
*A01H 5/00* (2006.01)

(52) U.S. Cl. ..... Plt./332

(58) Field of Classification Search ..... Plt./332
See application file for complete search history.

*Primary Examiner*—Wendy C. Haas
*Assistant Examiner*—Georgia Helmer
(74) *Attorney, Agent, or Firm*—Jondle & Associates, P.C.

(57) ABSTRACT

A new cultivar of *pelargonium* particularly characterized by having deep-purple, single-type flowers, floriferous with medium-sized inflorescences on relatively short peduncles, deep-green foliage with distinct zonation in the center of the leaves, medium to tall size, trailing, well-branched plant habit and an early flowering response, is disclosed.

2 Drawing Sheets

Genus and species: *Pelargonium peltatum* L'Héritier.
Variety denomination: 'Fisburg'.

BACKGROUND OF THE NEW PLANT

The present invention comprises a new and distinct cultivar of *pelargonium,* botanically known as *Pelargonium peltatum,* and hereinafter referred to by the cultivar name 'Fisburg'. The new cultivar is a product of a planned breeding program which had the objective of creating new ivy geraniums in a variety of colors, having large, single-type flowers and suitable for the range of vigorously growing varieties. 'Fisburg' was discovered as a seedling resulting from the cross of the female parent 'K98-3029-14' (unpatented), a proprietary *pelargonium* plant having purple, semi-double flowers and the male parent 'Nelson Reip' (unpatented), a commercial *pelargonium* plant having deep-purple, single-type flowers.

The new cultivar was created in 2000 in Hillscheid, Germany and has been asexually reproduced repeatedly by vegetative cuttings in Galdar, Gran Canaria, Spain, and Hillscheid, Germany over a five-year period. It has been found to retain its distinctive characteristics through successive asexual propagations. 'Fisburg' reproduces true to type in successive generations of asexual reproduction.

Plant Breeder's Rights for this cultivar were applied for in Germany on Apr. 4, 2005 and in Canada on Apr. 20, 2005.

SUMMARY OF THE INVENTION

The following are the most outstanding and distinguishing characteristics of this new cultivar when grown under normal horticultural practices in Hillscheid, Germany.

1. Deep-purple, single-type flowers with good stability of flower color;
2. Floriferous with medium to large inflorescences;
3. Deep-green foliage with distinct zonation in the center of the leaf;
4. A medium-sized to tall, well-branched, trailing plant habit; and
5. An early-season flowering response.

DESCRIPTION OF THE PHOTOGRAPHS

This new *pelargonium* plant is illustrated by the accompanying photographs which show overall plant habit including inflorescences, buds, and foliage of the plant; the colors shown are as true as can be reasonably obtained by conventional photographic procedures. The photographs are of three 30-week-old plants in a hanging basket in early September and grown under greenhouse and outdoor conditions which approximate those generally used in commercial practice.

DESCRIPTION OF THE NEW CULTIVAR

Figure 1:
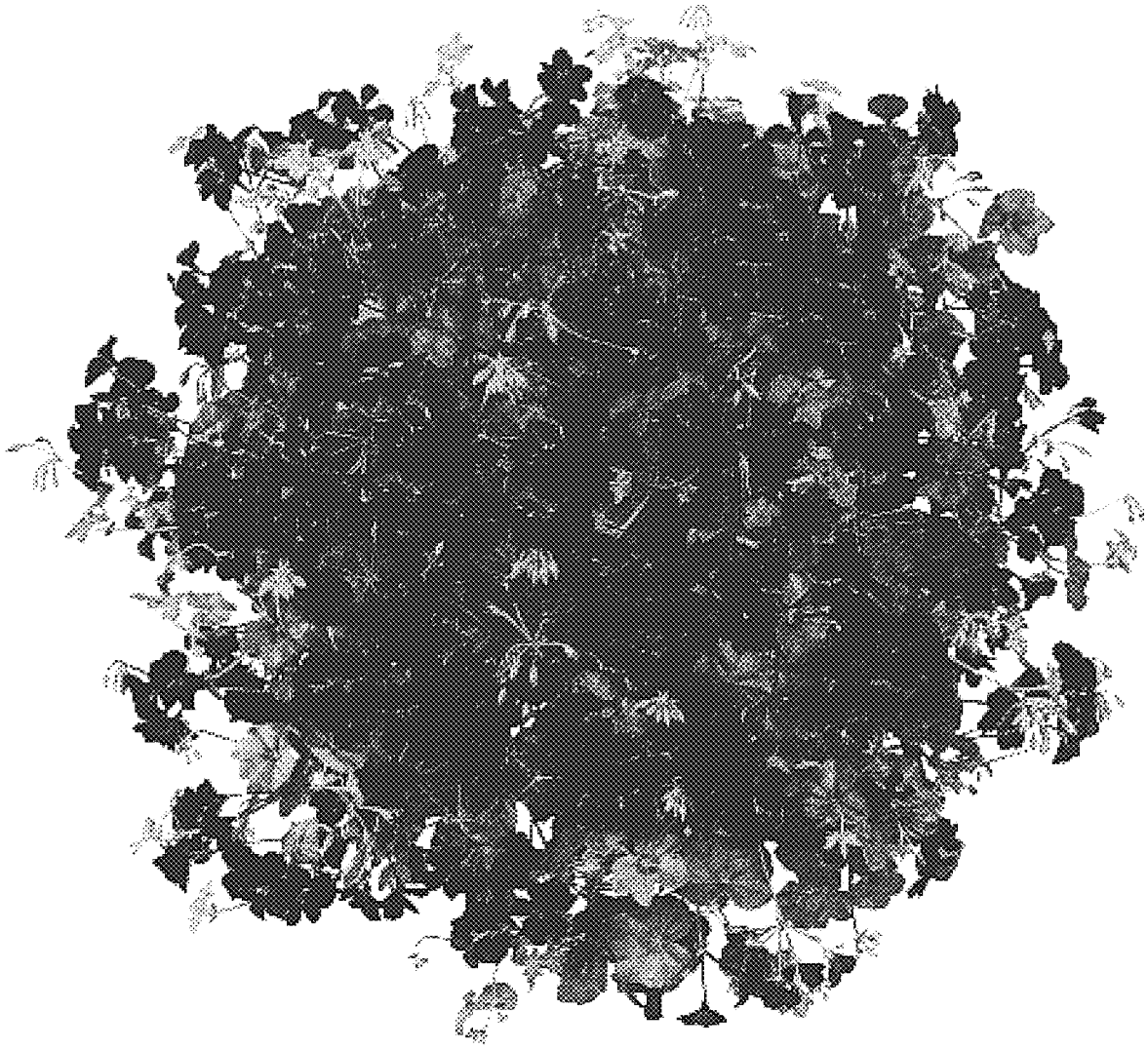
FIG. 1 shows the overall plant habit with blooms, buds and foliage.
Figure 2:
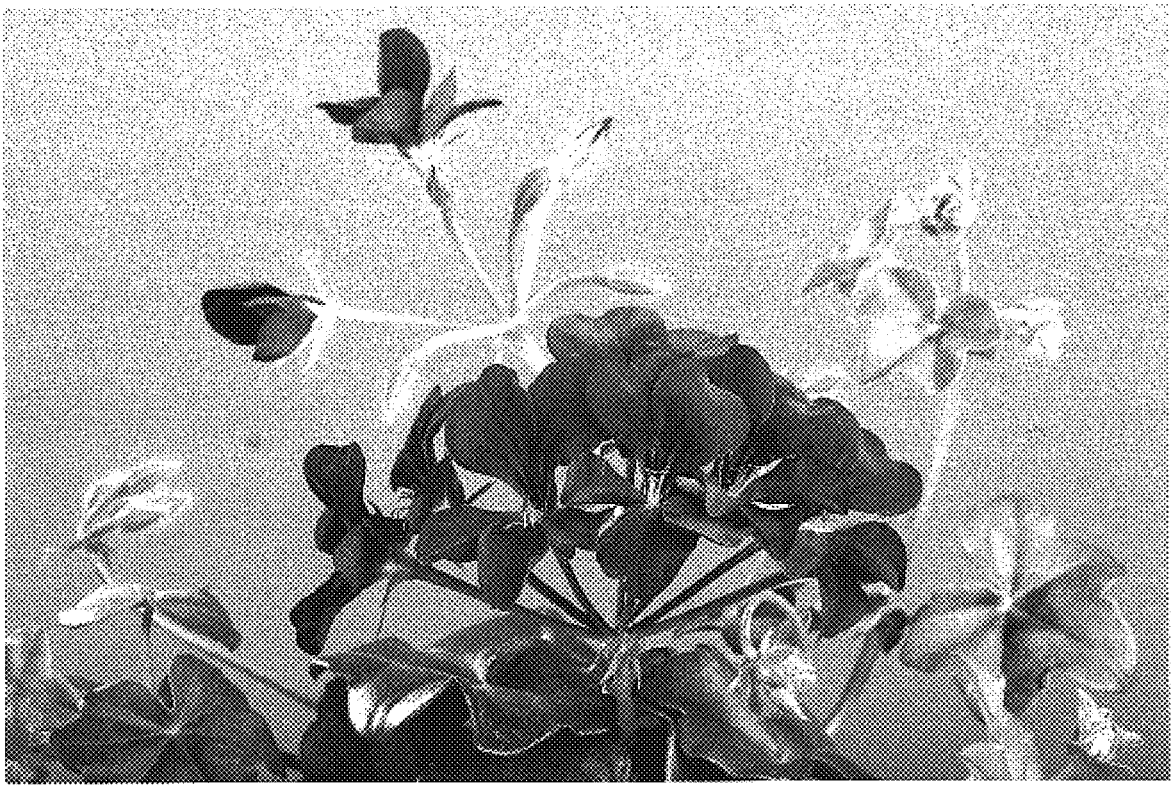
FIG. 2 shows a close-up view of an inflorescence taken under artificial light.

The following detailed description sets forth the distinctive characteristics of 'Fisburg'. The data which define these characteristics were collected from asexual reproductions carried out in Hillscheid, Germany. The plant history was taken on 15-week old plants, pinched once, in 12-cm pots in a greenhouse during late May. Color readings were taken under natural light in mid-May in the greenhouse. Color references are primarily to the RHS Colour Chart in The Royal Horticultural Society of London (RHS) (2001).

DETAILED BOTANICAL DESCRIPTION

Classification:
*Family.*—Geraniaceae.
*Botanical.*—*Pelargonium peltatum* L'Héritier.
*Common name.*—Ivy geranium.

Parentage:
*Female parent.*—'K98-3029-14' a proprietary *pelargonium* plant having purple, semi-double flowers (unpatented).
*Male parent.*—'Nelson Reip', a commercial *pelargonium* plant having deep-purple, single-type flowers (unpatented).

Plant:

*Form.*—Shrub, self-branching, trailing habit.

*Branching habit.*—6 to 8 branches per plant.

*Height (measured from base of the stem to the tips of the branches, excluding the inflorescence).*—14.2 cm for a 15-week-old plant.

*Width (plant diameter).*—23.3 cm for a 15-week-old plant.

*Plant spread at end of summer (about 30 weeks ld).*—80 cm to 90 cm.

*Time to produce a finished flowering plant.*—About 11 to 12 weeks.

*Outdoor plant performance.*—Plants continuously flower; a count in late summer of 30-week old plants in Hillscheid, Germany showed about 25–30 inflorescences per plant.

Leaves:

*Arrangement.*—Alternate; opposite at flowering branches.

*Immature leaf color.*—Medium-green. Upper surface: RHS 137C. Lower surface: RHS 138A.

*Mature leaf color.*—Deep-green. Upper surface: RHS 137A to RHS 137B. Lower surface: RHS 137D.

*Zonation color.*—RHS 166A (brown) with medium distinctness.

*Zonation diameter.*—Inner diameter of ring: 0.5 cm to 0.7 cm. Band of belt of zonation: 0.5 cm to 1.0 cm.

*Size.*—Length: 4.0 cm. Width: 6.1 cm.

*Shape.*—Ivy-shaped with 5 lobes and with the lowest lobes often overlapping.

*Apex.*—Rounded with lobes.

*Base.*—Cordate.

*Margin.*—Entire.

*Texture.*—Upper surface is leathery and somewhat glossy.

*Petioles.*—Color: RHS 143B (light-green). Length: 2 cm to 4 cm. Diameter: 0.25 cm. Texture: Sparse pubescence, nearly glabrous.

Stems:

*Stem color.*—RHS 143B (green).

*Length.*—20 cm.

*Diameter.*—0.4 cm.

*Internode length.*—0.5 cm to 1.0 cm.

*Texture.*—Appears smooth, slight pubescence.

Flower bud: (just before petals unfold).

*Shape.*—Elliptical, narrow.

*Size.*—Length: 2.4 cm. Width: 1.0 cm.

*Color of sepals.*—RHS 143A (grass-green).

*Color of petals.*—RHS 187D.

Inflorescence:

*Inflorescence type.*—An umbel composed of 9 to 11 flowers.

*Umbel.*—Shape: Irregular, part of a semi-sphere. Diameter: 11.0 cm. Height (depth): 5.8 cm.

*Lastingness of umbel on the plant.*—About 16 days.

*Peduncle.*—Color: RHS 143A (grass-green). Length: 12.5 cm. Diameter: 0.2 cm to 0.25 cm. Texture: With weak pubescence.

*Pedicel.*—Color: Partly RHS 143B (light-green), partly strong infusion with anthocyanin. Anthocyanin color: RHS 183C. Length: 3.9 cm. Diameter: 0.15 cm. Texture: Pubescent.

Corolla:

*Shape of corolla.*—Zygomorphic, with the petals not overlapping.

*Form.*—Single-type.

*Diameter.*—4.5 cm.

*Number of petals.*—5.

*Petaloids.*—None.

*Lastingness of individual flowers on plant.*—6 days at 18° C.

*Fragrance.*—None.

Petals:

*Apex.*—Rounded to nearly truncate or retuse.

*Base.*—Acuminate.

*Margin.*—Entire.

*Texture.*—Smooth, slightly glossy.

*Upper petals.*—Shape: Spatulate. Length: 3.0 cm to 3.2 cm. Width: 1.6 cm to 1.9 cm. Color: Upper surface: RHS 59A (deep purple) with blackish overtone. Lower surface: Near RHS 61A. Markings: Strong blackish veins, RHS 200A to RHS 202A.

*Lower petals.*—Shape: Obovate. Length: 2.4 cm to 2.6 cm. Width: 1.7 cm to 1.8 cm. Color: Upper surface: RHS 59B. Lower surface: Between RHS 61A to RHS 61B. Markings: Absent.

Sepals:

*Number.*—5.

*Color.*—For the lower surface, RHS 143A (grass-green), for the upper (initially inner) surface RHS 143C, largest sepal with RHS 178A (reddish-brown) for the lower surface.

*Length.*—1.2 cm to 1.5 cm.

*Width.*—Largest upper sepal: 0.5 cm. Other sepals: 0.3 cm.

*Shape.*—Ensiform to lanceolate.

*Apex.*—Acute.

*Base.*—Fused.

*Margin.*—Entire.

*Texture.*—Covered with long hairs.

Reproductive organs:

*Androecium.*—Number of anthers: 7. Filament length: 0.8 cm to 1.3 cm. Filament color: RHS 155D (white) to RHS 61C at the upper end. Pollen color: RHS 28A (orange). Pollen amount: Moderate.

*Gynoecium.*—Pistil: Number: 1. Length: 0.9 cm. Stigma color: RHS 59A (deep-purple). Stigma shape: 5-to-6 lobed. Style color: RHS 155D (whitish) to RHS 76B (pale-purple). Style length: 0.4 cm to 0.5 cm. Style shape: Filiform (filament-like) with the lobes of the stigma slanting upright, later at right angles.

Fruit and seed set: A little, mainly from late summer to fall: whole fruit with 'beak' about 3.8 cm in length, often with 4 seeds; seed grain 0.5 cm to 0.6 cm in length; 0.3 cm in diameter, with spiral 'tail'.

Disease and insect resistance: No particular resistance or susceptibility has been observed; very little botrytis due to the single-type, self-cleaning flowers and open inflorescence shape.

COMPARISON WITH PARENTAL AND COMMERCIAL CULTIVARS

'Fisburg' differs from the female parent 'K98-3029-14' (unpatented) by having single-type flowers, while 'K98-3029-14' has semi-double flowers. In addition, 'Fisburg' has a less compact plant habit than 'K98-3029-14'.

'Fisburg' differs from the male parent 'Nelson Reip' (unpatented) by having wider, rounder petals and a lower tendency for the flower color to fade then 'Nelson Reip'. In addition, 'Fisburg' grows somewhat less vigorously and has shorter internodes than 'Nelson Reip'.

'Fisburg' differs from the commercial variety 'Fisblipur' (U.S. Plant Pat. No. 15,214) by having a less bluish, more deep purple-red hue of flower color than 'Fisblipur'. In addition, 'Fisburg' grows less vigorously than 'Fisblipur'.

'Fisburg' differs from the commercial variety 'Fisruby' (U.S. Plant Patent Pending) by having more bluish, single-type flowers, while 'Fisruby' has less bluish, double flowers.

I claim:

1. A new and distinct cultivar of *pelargonium* plant as shown and described herein.

* * * * *